(12) United States Patent
Carlson et al.

(10) Patent No.: US 9,028,896 B2
(45) Date of Patent: May 12, 2015

(54) **PRODUCTION OF COTTAGE CHEESE BY USING *STREPTOCOCCUS THERMOPHILUS***

(75) Inventors: Morten Carlson, Hilleroed (DK); Thomas Janzen, Frederiksberg (DK)

(73) Assignee: Chr. Hansen A/S, Hoersholm (DK)

( * ) Notice: Subject to any disclaimer, the term of this patent is extended or adjusted under 35 U.S.C. 154(b) by 388 days.

(21) Appl. No.: 13/379,569

(22) PCT Filed: Jul. 9, 2010

(86) PCT No.: PCT/EP2010/059903
§ 371 (c)(1),
(2), (4) Date: Dec. 20, 2011

(87) PCT Pub. No.: WO2011/004012
PCT Pub. Date: Jan. 13, 2011

(65) Prior Publication Data
US 2012/0100252 A1 Apr. 26, 2012

(30) Foreign Application Priority Data

Jul. 10, 2009 (EP) ..................................... 09165147
Aug. 26, 2009 (EP) ..................................... 09168730

(51) Int. Cl.
*A23C 9/12* (2006.01)
*A23C 19/032* (2006.01)
*A23C 19/076* (2006.01)
*C12R 1/46* (2006.01)

(52) U.S. Cl.
CPC ........... *A23C 19/0323* (2013.01); *A23C 19/076* (2013.01); *A23Y 2240/75* (2013.01); *C12R 1/46* (2013.01)

(58) Field of Classification Search
CPC ............ A23C 9/00; A23C 9/12; A23C 19/00; A23C 19/02; A23C 19/032; A23C 19/0323; A23C 19/076; A23Y 2240/75; C12R 1/46

USPC ................................ 426/34, 36, 38, 580, 582
See application file for complete search history.

(56) References Cited

U.S. PATENT DOCUMENTS

| | | | |
|---|---|---|---|
| 3,298,836 A | 1/1967 | Ernstrom | |
| 5,116,737 A | 5/1992 | McCoy | |
| 6,962,721 B1 | 11/2005 | Sepulchre et al. | |
| 2006/0240539 A1 | 10/2006 | Horvath et al. | |
| 2012/0288586 A1* | 11/2012 | Peterson | 426/39 |
| 2014/0134292 A1* | 5/2014 | Petersen | 426/36 |
| 2014/0154389 A1* | 6/2014 | Petersen | 426/582 |

FOREIGN PATENT DOCUMENTS

| | | |
|---|---|---|
| SU | 1785633 A1 * | 1/1993 |
| WO | WO-91/00690 | 1/1991 |
| WO | WO-2007/144770 A2 | 12/2007 |
| WO | WO-2008/040734 A1 | 4/2008 |
| WO | WO-2008/148561 A1 | 12/2008 |
| WO | WO-2010/066907 A1 | 6/2010 |

OTHER PUBLICATIONS

Case History Clinic: Gold Spot Dairy Boosts Cottage Cheese Sales, Dairy and Ice Cream Field, vol. 156, 1973, pp. 46-47.
D. Mora et al., "Characterization of urease genes cluster of *Streptococcus thermophilus*", Journal of Applied Microbiology, 2004, 96, 209-219.
D. Mora et al., "Genetic diversity and technological properties of *Streptococcus thermophilus* strains isolated from dairy products", Journal of Applied Microbiology, 2002, 93, 278-287.
International Search Report PCT/EP2010/059903 dated May 26, 2011.
Wendy Tinson et al., "Metabolism of *Streptococcus thermophilus*", The Australian Journal of Dairy Technology, Mar. 1982, pp. 17-21.

\* cited by examiner

*Primary Examiner* — Leslie Wong
(74) *Attorney, Agent, or Firm* — Foley & Lardner LLP

(57) ABSTRACT

A method for producing cottage cheese by using *Streptococcus thermophilus* bacteria.

14 Claims, 3 Drawing Sheets

Figure 1:
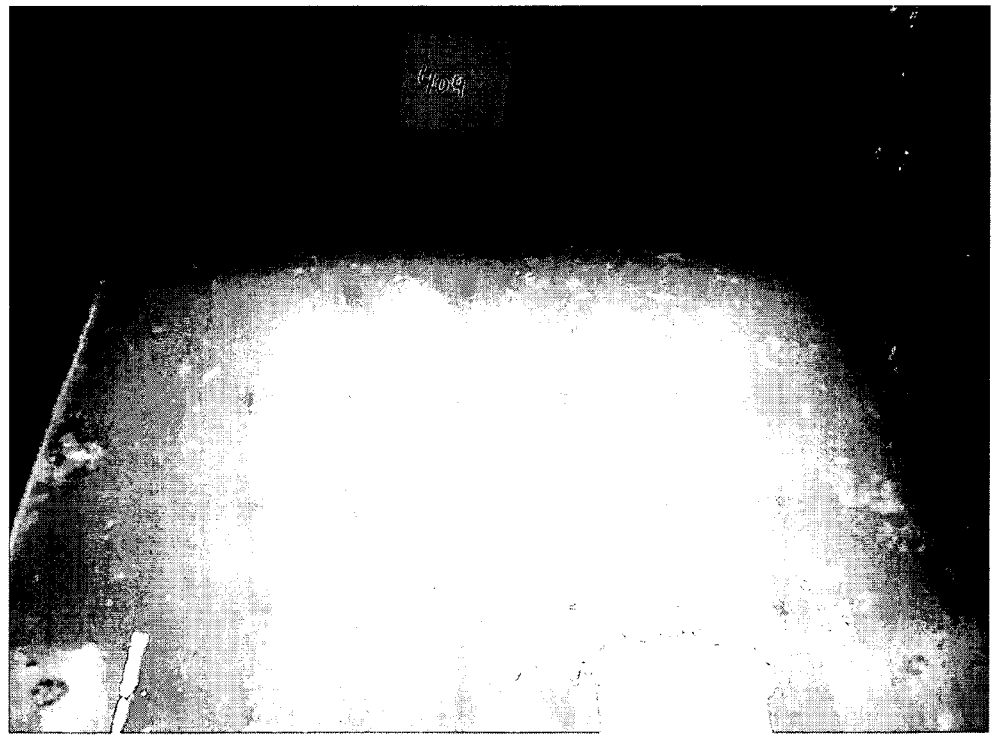

Cottage cheese vat - produced with the ur(-) mutant CHCC9908.

The cheese curd depth both in the middle and at the corners were at both places 7-8 cm below the whey surface.

Control cottage cheese vat - made with the ur(+) strain.

The cheese curd was right at the surface of the whey in the corners and in the middle it was about 2.5 cm below the surface (see arrows).

Control cottage cheese vat - made with the ur(+) strain.

The floating cheese curd was right at the surface of the whey - see arrows.

PRODUCTION OF COTTAGE CHEESE BY USING STREPTOCOCCUS THERMOPHILUS

CROSS-REFERENCE TO RELATED APPLICATIONS

This application is the U.S. National Phase of PCT/EP2010/059903 filed Jul. 9, 2010, which claims priority from European Patent Application No. 09165147.1 filed Jul. 10, 2009, and which also claims priority from European Patent Application No. 09168730.1 filed Aug. 26, 2009. Each of which is incorporated herein by reference in entirety.

FIELD OF THE INVENTION

The present invention relates to a method for producing cottage cheese by using Streptococcus thermophilus bacteria.

BACKGROUND ART

Lactic acid bacteria (LAB) are intensively used in the dairy industry for making different animal milk fermented products such as cottage cheese. Cottage cheese accounts for approx. 700,000 tons of the world's 18.2 million tons consumed in 2008. In North America cottage cheese makes up approx. 12% of all cheese. Normally, cottage cheese cultures comprise homofermentative Lactococcus strains such as e.g. Lactoccus lactis strains.

Relatively recently (within the last 3-5 years) Streptococcus thermophilus (ST) has been added to cottage cheese cultures. Addition of S. thermophilus may give a shorter fermentation time (e.g. shortened to around 4-5 hours). S. thermophilus strains are generally capable of expressing the enzyme urease (EC 3.5.1.5), which is an enzyme that catalyzes the hydrolysis of urea into carbon dioxide ($CO_2$) and ammonia ($NH_3$). Milk comprises urea—accordingly, due to the production of the base $NH_3$ by S. thermophilus there may be a temporary decrease in acidification speed during the fermentation of milk. In relation to this problem—$NH_3$ induced temporary decrease in acidification speed—U.S. Pat. No. 6,962,721B1 (Texel, FR) describes that by using S. thermophilus that e.g. are not producing active urease enzyme (so-called "ur(−) strains") one may get an improved acidification kinetic profile.

As technological background prior art that describes prior art known methods to make cottage cheese as such—may herein be mentioned U.S. Pat. No. 3,298,836 (published 1967); WO91/00690A1 and the article ("Gold Spot Dairy boost cottage cheese sales", Dairy and Ice Cream Field, vol. 156, no. 6, 1973, pages 46-47).

U.S. Pat. No. 5,116,737 relates to bacteria that are producing active urease enzyme (may be termed "ur(+) strains").

SUMMARY OF THE INVENTION

The problem to be solved by the present invention is to provide an IMPROVED method for making cottage cheese—in particular a method that gives less of so-called floating cheese curd problems (see below for further discussion). Also, the present invention provides a method for increasing the yield of cottage cheese, esp. cottage cheese made using a Streptococcus thermophilus strain.

The solution may be seen as based on that the present inventors have identified that:

(1): Use of Streptococcus thermophilus (ST) for making cottage cheese may give a floating cheese curd problem—according to our knowledge this S. thermophilus related floating cheese curd problem has NOT been described in the art—i.e. it may be considered a hitherto unrecognized problem;

(2): Once the inventors recognized the floating cheese curd problem—they identified that it could be solved by using S. thermophilus bacteria that are not able to release ammonia from urea (herein termed S. thermophilus "ur (−) strains").

It is here relevant to note that U.S. Pat. No. 6,962,721B1 (discussed above) does NOT mention or suggest anything of herein relevance with respect to a possible floating cheese curd problem and the term "cottage cheese" is NOT mentioned at all in U.S. Pat. No. 6,962,721B1. Further, U.S. Pat. No. 6,962,721 describes in Example 4 (column 9-10) production of "Solubilized Soft Cheese" —the Soft Cheese is made using ST Ur(+) or ST Ur(−). This is the ONLY working example in U.S. Pat. No. 6,962,721 that relates to production of cheese. Without being limited to theory, it is believed that even if the authors of U.S. Pat. No. 6,962,721 would have measured floating curd—as discussed herein—they would NOT have been able to identify the herein—for the FIRST time—observed floating curd problem. As discussed further below, the reason for this may essentially be explained due to that the process for making Soft Cheese is fundamentally different from cottage cheese.

In working examples herein it is demonstrated that by using a S. thermophilus ur(−) strain for cottage cheese production one gets significant LESS floating cheese curd as compared to use of the corresponding wild-type ur(+) strain—compare e.g. FIG. 1 herein showing that use of ur(−) gave a cheese curd depth 7-8 cm below the whey surface with FIG. 2 herein showing that use of ur(+) gave a control vat where the cheese curd was right at the surface of the whey.

Below are discussed herein relevant process parameters for making cottage cheese.

Cottage Cheese Production in General

The herein relevant well known process steps for making cottage cheese may be summarized in the following way:

Step 1:

There is used a relatively long fermentation period in the cheese vat with relevant lactic acid bacteria (LAB) (normally homofermentative Lactococcei/Lactococcus) to get a pH drop from around pH 6.6 (i.e. pH of milk) to around pH 4.65. Normally one needs from 6-12 hours, at 30-35° C. of fermentation to reach the pH of around 4.65;

Step 2:

When the pH has reached around 4.65 —the coagulum is cut into cheese curd in order to separate the whey from the cheese curd. The result of this is that the cheese curd drops to the bottom of the cheese vat with the whey above (see e.g. FIG. 1). This cut step normally takes 5-10 minutes and the cheese curd rests for 20-30 minutes before scalding (heating) step 3;

Step 3:

Scalding (heating) is done in order to stop the LAB fermentation process and to increase the syneresis (separation of the whey) of the cheese curd in order to get a firmer cheese curd.

Scalding is done in the cheese vat at the surface of the whey by e.g. a steam-injector lowered down right below the whey surface and above the cheese curd (see FIG. 1).

The steam causes the whey and cheese curd to "move around" in the cheese vat and therefore causes the cheese curd to "get up" to the surface again.

The scalding is normally done in three separate steps in order to gradually go from the fermentation temperature of 35° C. to around 60° C.

Normally the "moving around" cheese curd will settle down in the vat during the rest period between the three separate scalding steps.

The steam-injector has filters around the steam "out-put". If these filters get blocked by e.g. floating curd then the whey cannot pass the filters in order to be scalded (heated) by steam from the steam "out-put". Further, if the filters get blocked the steam cannot "get out" to the whey and it will therefore create a kind of an "air-bubble" causing the steam-injector to be "lifted out" of the whey.

ST Ur(+)—Cottage Cheese—Floating Problem

As discussed above, "historically" it is common only to use homofermentative *Lactococcei* for the cottage cheese fermentation.

Said in other words, cottage cheese cultures "historically" comprised only homofermentative *Lactococcei*.

Relatively recently (within the last 3-5 years) *Streptococcus thermophilus* (ST) has been added to cottage cheese cultures.

As known in the art, addition of *S. thermophilus* may give a shorter fermentation time (e.g. shortened to 4-5 hours).

According to the knowledge of the present inventors—hitherto cottage cheese producers have always used *S. thermophilus* with an active urease—i.e. so-called ur(+) phenotype strains.

The present invention is based on that the present inventors identified that the use of *S. thermophilus* strains gave an unexpected floating curd problem.

Figure 2:
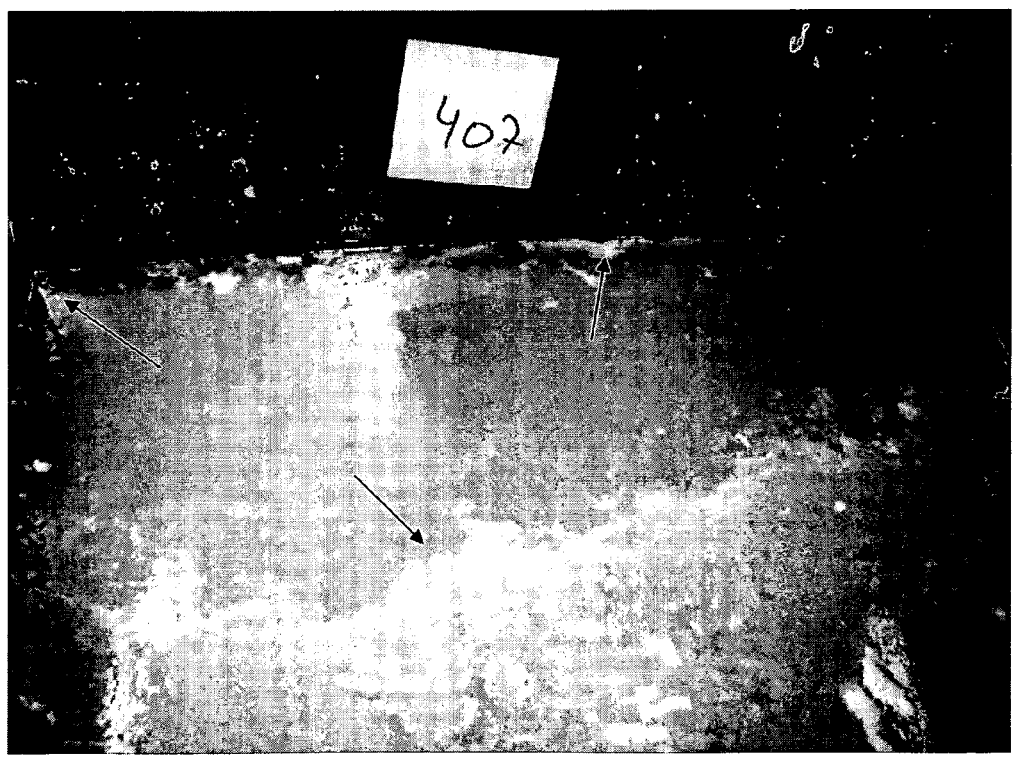

As can be seen in FIG. 2, the observed floating curd problem was e.g. so extensive that the cheese curd in the vat was right at the surface of the whey in the corners, and in the middle it was about 2.5 cm below the surface.

The herein—for the first time—observed floating curd problem may be seen as a "real-life" commercially very important problem.

For a lot of cottage cheese producers this means that they have to use extra man-power, and there will be significant yield loss, as the floating curd will be trapped in filters when scalding the cheese curd—see step 3 discussions above.

Soft Cheese Production in General—NO Floating Curd Problem

The above discussed prior art document U.S. Pat. No. 6,962,721 describes in Example 4 (column 9-10) production of "Solubilized Soft Cheese"—the Soft Cheese is made using ST Ur(+) or ST Ur(−).

Without being limited to theory, it is believed that even if the authors of U.S. Pat. No. 6,962,721 would have measured floating curd—as discussed herein—they would NOT have been able to identify the herein observed floating curd problem.

The reason for this may essentially be explained by that the process for making Soft Cheese is fundamentally different from making cottage cheese.

Herein relevant fundamental differences include:
(a): For Soft Cheese, there is NO long fermentation period in the cheese vat—contrary to the long fermentation period for cottage cheese as discussed under Step 1 above. The fermentation period for Soft Cheese in the cheese vat is only until pH reaches 6 to 6.3, which normally only takes about 2 hours;
(b): For Soft Cheese, there is NO Scalding (heating) in the cheese vat—i.e. contrary to the Scalding (heating) in the cheese vat for cottage cheese as discussed under Step 3 above.

As discussed above, in working examples herein it is demonstrated that by using a *S. thermophilus* ur(−) strain for cottage cheese production one gets significantly LESS floating cheese curd as compared to use of the corresponding wild-type ur(+) strain.

Accordingly, a first aspect of the invention relates to a method for producing cottage cheese comprising following steps:
(a): inoculating milk with *Streptococcus thermophilus* bacteria, characterized by that the *S. thermophilus* bacteria are not able to release ammonia from urea (herein termed *S. thermophilus* "ur(−) bacteria");
(b): fermenting the milk with the bacteria; and
(c): making further adequate steps to finally end up with the produced cottage cheese.

As described below—herein one may define/analyze if a *S. thermophilus* bacterium of interest is a ur(−) strain or not by using the from U.S. Pat. No. 6,962,721 known plate assay of working Example 1 herein—i.e. a *S. thermophilus* ur(−) bacterium is forming a yellow colony in the Petri Dishes plate assay of Example 1 herein.

Accordingly, the sentence of first aspect reading "not able to release ammonia from urea" may be understood as a "descriptive" sentence—i.e. the main point is if a *S. thermophilus* bacterium of interest is forming a yellow colony in plate assay of Example 1 herein or not.

In some places herein it may be said that ur(−) bacteria are "not producing active urease enzyme". In line of above—and as understood by the skilled person in the present context—this wording/sentence may also be understood as a "descriptive" sentence—i.e. the main point is if a *S. thermophilus* bacterium of interest is forming a yellow colony in plate assay of Example 1 herein or not.

As understood—a *S. thermophilus* bacterium may be ur(−) in different ways—e.g. by not producing active urease enzyme or by e.g. not being capable of taking up urea from media or by not being able to excrete ammonia etc—in all these cases the end result would be that the ur(−) bacterium would not be able to release ammonia from urea as described in a "descriptive" manner in first aspect above.

Embodiments of the present invention are described below, by way of examples only.

DRAWING

FIG. 1: Cottage cheese vat—produced with the ur(−) mutant CHCC9908. The cheese curd depth both in the middle and at the corners were at both places 7-8 cm below the whey surface. See working example 2 herein for further details.

FIG. 2: Control cottage cheese vat—made with the ur(+) strain. The cheese curd was right at the surface of the whey in the corners and in the middle it was about 2.5 cm below the surface (see arrows). See working example 2 herein for further details.

Figure 3:
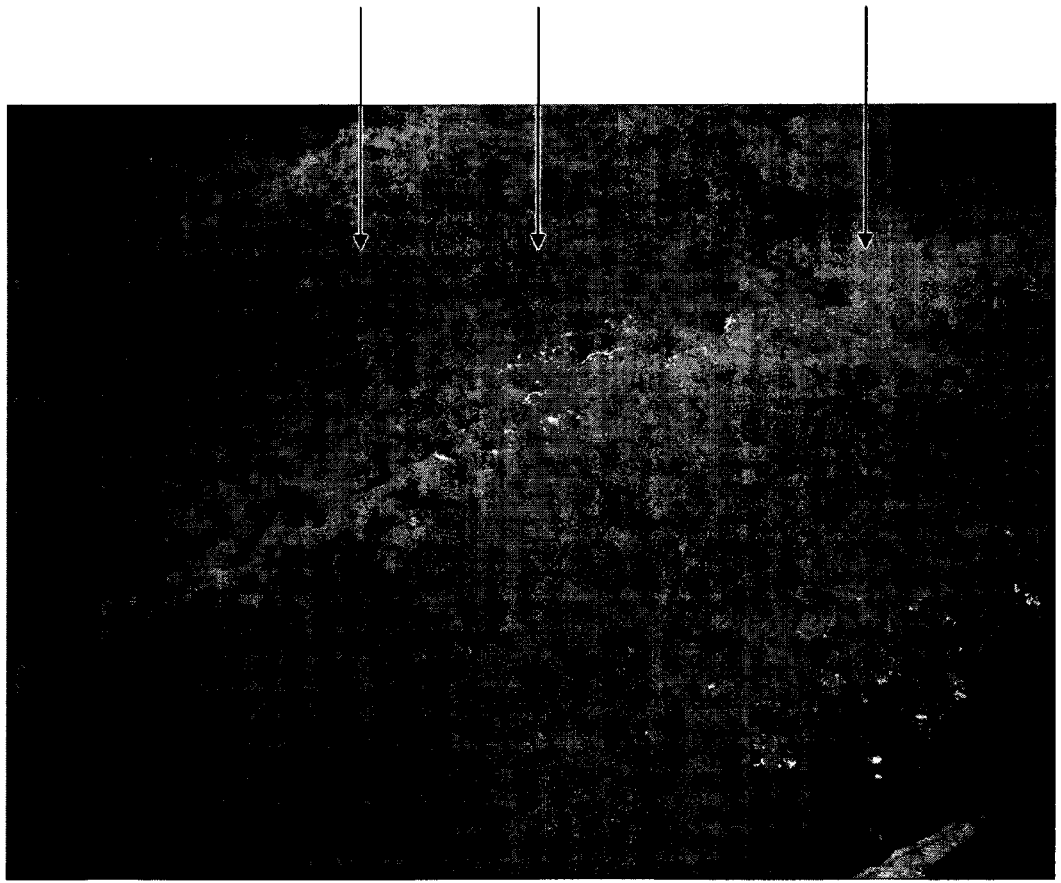

FIG. 3: Control cottage cheese vat—made with the ur(+) strain. The floating cheese curd was right at the surface of the whey (see arrows).

DETAILED DESCRIPTION OF THE INVENTION

Cottage Cheese

The skilled person of course knows if he is producing a cottage cheese or a different kind of cheese (e.g. a soft cheese).

Accordingly, it is submitted that there herein is no real need to further define/describe the term "cottage cheese".

However, for information a short description of cottage cheese is included below.

Cottage cheese may be seen as a cheese curd product with a mild flavor. It is normally drained, but normally not pressed so some whey may remain and the individual curds may remain loose.

Different styles of cottage cheese are made from milks with different fat levels and in small curd or large curd preparations.

Cottage cheese may be eaten straight. It is also eaten with fruit, with fruit puree, on toast, in green salads,—or as an ingredient in recipes like jello salad and various desserts. It can be used to replace grated cheese or ricotta cheese in most recipes (such as lasagna).

The term "cottage cheese" is believed to have originated because the simple cheese was usually made in cottages from any milk left over after making butter. The term was first used in 1848.

Inoculating Milk with Bacteria—Step (a) of First Aspect

Step (a) of first aspect relates to inoculating milk with *S. thermophilus* bacteria.

Preferably, the milk is cow milk or goat milk—normally cow milk is used.

The term "bacteria"—in the first aspect described herein—is in plural since it makes no sense to here talk about inoculating milk with only one single bacterium. However, it is evident that the inoculation may e.g. be done by using e.g. $10^8$ cfu/ml bacteria of the same bacterial strain—e.g. the *S. thermophilus* ur(−) bacterium as used in working examples herein.

Further, the milk may be inoculated with other bacteria than the herein essential *S. thermophilus* ur(−) bacteria.

As discussed above, cottage cheese cultures normally comprise *Lactococcus* strains such as e.g. *Lacotoccus lactis* strains.

Accordingly, preferably the milk in step (a) of first aspect is also inoculated with *Lactococcus* bacteria, preferably *Lactoccus lactis* bacteria.

Lactic acid fermentation breaks the pyruvate down into lactic acid. These lactic acid bacteria can be classed as homofermentative, where the end product is mostly lactate, or heterofermentative, where some lactate is further metabolized and results in carbon dioxide, acetate or other metabolic products.

For cottage cheese production is normally used homofermentative *Lactococcus* bacteria and it is therefore also preferred herein.

Preferably, there is inoculated at least $10^4$ cfu/ml of bacteria (preferably *Lactococcus* bacteria) to the milk, such as from $10^4$ to $10^{13}$ cfu/ml of bacteria (preferably *Lactococcus* bacteria) to the milk—more preferably there is inoculated from $10^8$ to $10^{12}$ cfu/ml of bacteria (preferably *Lactococcus* bacteria) to the milk.

The skilled person of course knows what the preferred amount of bacteria could be for production of a particular cottage cheese of interest.

*S. thermophilus* ur(−) Bacteria

An essential element of the present invention is to use *S. thermophilus* ur(−) bacteria for inoculation of milk in step (a) of first aspect.

As discussed above, *S. thermophilus* ur(−) bacteria as discussed herein are characterized by that the *S. thermophilus* bacteria are not able to release ammonia from urea.

As discussed above, it is known in the art to make such *S. thermophilus* ur(−) bacteria—see for instance U.S. Pat. No. 6,962,721 (Texel, FR) discussed above.

Accordingly, in the present context it may be seen as routine work for the skilled person to make such *S. thermophilus* ur(−) bacteria—further the *S. thermophilus* ur(−) bacteria may be made with a required/wanted milk acidification profile/kinetic (see e.g. Example 3 of U.S. Pat. No. 6,962,721).

Accordingly, suitable examples of herein useful *S. thermophilus* ur(−) bacteria could be the *Streptococcus thermophilus* strain 298-K registered at the CNCM under number 1-2311 (see claim 6 of U.S. Pat. No. 6,962,721) or the *Streptococcus thermophilus* strain 298-10 registered at the CNCM under number 1-2312 (see claim 7 of U.S. Pat. No. 6,962,721).

As evident, other suitable examples of herein useful *S. thermophilus* ur(−) bacteria could be the *S. thermophilus* ur(−) strain CHCC9908-CHCC9908 was used in working Examples as discussed below (it is available upon request at Chr. Hansen A/S—i.e. applicant of present invention).

Further, in the present context it may be seen as routine work for the skilled person to identify whether or not a particular *S. thermophilus* strain of interest is a ur(−) strain or not.

A suitable plate assay to test for urease activity is provided in Example 1 of U.S. Pat. No. 6,962,721 (see column 4)—relevant text of this Example 1 of U.S. Pat. No. 6,962,721 plate assay is provided as working Example 1 herein.

As can se seen in Example 1 of U.S. Pat. No. 6,962,721 and working Example 1 herein—the plate assay is simple and the skilled person can routinely identify if a *S. thermophilus* strain is ur(−) or ur(+)—as said in Example 1 of U.S. Pat. No. 6,962,721, lines 52-54: "The ur(+) clones form blue-coloured halos owing to the production of ammonia, whereas the ur(−) clones form yellow colonies.".

Accordingly, a *S. thermophilus* ur(−) bacterium may herein be understood as a bacterium that is a ur(−) strain in the Petri Dishes plate assay of Example 1 of U.S. Pat. No. 6,962,721 (reproduced herein as working Example 1)—i.e. a *S. thermophilus* ur(−) bacterium is forming a yellow colony in the Petri Dishes plate assay of Example 1 herein.

As known to the skilled person one may routinely select/identify herein suitable *S. thermophilus* ur(−) bacteria by use of e.g. the above discussed plate assay—for instance one may start from a suitable ur(+) wild-type strain, mutate this by e.g. use of a mutagen and use the plate assay to select/identify *S. thermophilus* ur(−) clones/strains.

As evident to the skilled person, such selected/identified "random" ur(−) mutants may comprise mutation(s)/deletion(s) at many herein relevant places of the bacterial genome—e.g. within a gene encoding for the urease enzyme or e.g. in relevant promoters outside the coding part of a gene as such.

In the present context, it may be seen as relatively "irrelevant", where such relevant mutation(s)/deletion(s) could be in a herein suitable *S. thermophilus* ur(−) bacterium—the main point is that such ur(−) mutants can routinely be made as discussed herein.

Preferably, there is inoculated at least $10^4$ cfu/ml of *S. thermophilus* ur(−) bacteria to the milk, such as from $10^4$ to $10^{13}$ cfu/ml of *S. thermophilus* ur(−) bacteria to the milk—more preferably there is inoculated from $10^8$ to $10^{12}$ cfu/ml of *S. thermophilus* ur(−) bacteria to the milk.

The skilled person knows what the preferred amount of *S. thermophilus* ur(−) bacteria could be for production of a particular cottage cheese of interest.

Fermenting the Milk with the Bacteria—Step (b) of First Aspect

Step (b) of first aspect relates to fermenting the milk with the bacteria.

As discussed above, the skilled person knows how to ferment milk with relevant bacteria to make a cottage cheese—accordingly, there is in the present context no need to describe this in great detail.

However, as discussed above—as known to the skilled person addition of *S. thermophilus* may give a shorter fermentation time—e.g. shortened to 4-5 hours as compared to the 6—12 hours without use of *S. thermophilus*.

Accordingly, the fermentation time in step (b) of the first aspect may be from 3 to 13 hours, more preferably from 3 to 10 hours, even more preferably from 3 to 7 hours and most preferably from 4 to 6 hours.

As understood by the skilled person—this fermentation time in step (b) of from e.g. 3 to 7 hours is related to the preferred amount of *S. thermophilus* ur(−) bacteria inoculated into the milk (see above)—i.e. one needs to add a relevant amount of *S. thermophilus* ur(−) bacteria to the milk in order to reach the relevant pH (around 4,65 as discussed above) within a preferred fermentation time (e.g. from 3 to 7 hours).

Further Adequate Steps to Make Cottage Cheese—Step (c) of First Aspect

Step (c) of first aspect relates to making further adequate steps to finally end up with the produced cottage cheese.

As discussed above, the skilled person knows how to make a cottage cheese—accordingly, there is no need to describe this in great detail in the present context.

As discussed above these further adequate steps include following steps that may be described as:

(i): when pH has reached around 4.65—the coagulum is cut into cheese curd in order to separate the whey from the cheese curd; and (ii): scalding (heating)—done in order to stop the bacteria fermentation process—normally done in the cheese vat at the surface of the whey by e.g. a steam-injector lowered down right below the whey surface and above the cheese curd.

Thus, an aspect of the present invention relates to method for producing cottage cheese comprising the following steps:

(a): inoculating milk with *Streptococcus thermophilus* bacteria, which are not able to release ammonia from urea (herein termed *S. thermophilus* "ur(−) bacteria");

(b): fermenting the milk with the bacteria.

It should be understood that the term "ur(−) bacteria" comprises bacteria which does not produce any (active) urease, as well as bacteria which produces a relative small amount of (active) urease, e.g. an amount that does not result in floating curd.

In an interesting embodiment, the invention relates to a method for producing cottage cheese comprising the following steps:

(a): inoculating milk with *Streptococcus thermophilus* bacteria, wherein all or a part of the said *Streptococcus thermophilus* bacteria are not able to release ammonia from urea (herein termed *S. thermophilus* "ur(−) bacteria");

(b): fermenting the milk with the bacteria. By "a part of" should be understood at least 50%, at least 70%, at least 90%, at least 95%, or at least 99% of the *S. thermophilus* bacteria are "ur(−) bacteria", measured as cfu/ml.

In a further interesting embodiment, the present invention relates to method for producing cottage cheese comprising the following steps:

(a): inoculating milk with *Streptococcus thermophilus* bacteria, wherein all or a part of the said *Streptococcus thermophilus* bacteria are not able to release ammonia from urea (herein termed *S. thermophilus* "ur(−) bacteria"), so that the total urease activity of the *Streptococcus thermophilus* bacteria culture is reduced by at least 50%, at least 70%, at least 90%, at least 95%, or at least 99%, compared to when a urease positive strain (e.g. the strain CNCM I-2980 (EP1604025)) is used as the only *Streptococcus thermophilus* bacteria;

(b): fermenting the milk with the bacteria.

Optionally, a method of the invention may comprise one or more steps (after step (b)) cutting the coagulum and/or heating and or washing the coagulum. Optionally, a milk coagulating enzyme may be added, e.g. rennet or chymosin, before, during or after step (b).

In a presently preferred embodiment, a method of the invention includes a step (c) comprising:

(i): when pH has reached around 4.65, (e.g. pH is in the range 4.0 to 5.0, in the range 4.4 to 4.8, or in the range 4.6 to 4.7) the coagulum is cut into cheese curd; and (ii): scalding (heating, cooking), e.g. done in the cheese vat at the surface of the whey by a steam-injector lowered down right below the whey surface and above the cheese curd. The curd may be cooked for up to 3 hours, and/or at a temperature above 45 degrees C., e.g. in the range 47-56 degrees C.

It is presently preferred that the milk is cow's milk.

In an interesting embodiment, the milk is inoculated with from $10^4$ to $10^{13}$ cfu/ml (cell forming units per ml) of *S. thermophilus* ur(−) bacteria, more preferably there is inoculated from $10^8$ to $10^{12}$ cfu/ml, or from 10E9 to 10E11 cfu/ml milk.

The fermentation time in step (b) may be from 3 to 7 hours.

In addition to the *S. thermophilus* ur(−) bacteria, the milk may also be inoculated with *Lactococcus* bacteria, preferably *Lacotoccus lactis* bacteria, such as homofermentative *Lactococcus* bacteria. The milk may be inoculated with from $10^4$ to $10^{13}$ cfu/ml of *Lactococcus* bacteria, or with from $10^8$ to $10^{12}$ cfu/ml of *Lactococcus* bacteria.

In a further aspect, the present invention relates to the use of *Streptococcus thermophilus* bacteria which are not able to release ammonia from urea (herein termed *S. thermophilus* "ur(−) bacteria) in a process for producing cottage cheese. The bacteria may be of strains selected from the group consisting of: 298-K (CNCM I-2311), 298-10 (CNCM I-2312), CHCC9908, and mutants of any of these.

In an other aspect, the invention relates to use of a *Streptococcus thermophilus* ur(−) mutant of a strain selected from the group consisting of: CNCM I-2980 (EP1604025A)), DSM21892 (WO10066907A), CNCM I-3617 (WO08040734A), DSM18344 (WO07144770A), CHCC4325, and DSM18111 (WO2008148561A, WO10023178A), in a process for producing cottage cheese.

The *Streptococcus thermophilus* ur(−) mutant of a strain selected from the group consisting of: CNCM I-2980 (EP1604025A)), DSM21892 (WO10066907A), CNCM I-3617 (WO08040734A), DSM18344 (WO07144770A), and DSM18111 (WO10023178A) is also an aspect of the present invention. A ur(−) mutant can routinely be made as disclosed herein.

In a last aspect, the present invention relates to cottage cheese obtainable (e.g. obtained) by a method of the invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXAMPLES

Example 1

Method of Culturing Ur(−) Bacteria on Petri Dishes

As discussed above—the text of this Example 1 is copied from Example 1, column 4 of U.S. Pat. No. 6,962,721.

An agar-based medium whose composition is shown in Table 1 is prepared and poured into Petri dishes of diameter equal to 9 cm.

TABLE 1

Composition of the culture medium.

| Tryptone<a> | 2.5 g |
|---|---|
| Pepsic meat peptone<a> | 2.5 g |
| Papainic soya peptone<a> | 5 g |
| Autolytic yeast extract<b> | 2.5 g |
| Meat extract<a> | 5 g |
| Sugar (glucose, lactose or saccharose) | 5 g |
| Sodium glycerophosphate•6H2O | 19 g |
| Magnesium sulphate | 0.25 g |
| Ascorbic acid | 0.5 g |
| Agar | 15 g |
| Distilled water | 1 liter |

<a>Blokar company
<b>Fischer Scientific company

If needed, a cofactor of urease can be added to this medium. Adjust the pH to 7.0 and autoclave for 15 minutes at 115° C.

The St. thermophilus cells to be analyzed are seeded on this medium so as to obtain around 100 colonies per Petri dish. The culture take place under anaerobic conditions at a temperature of 35-45° C., preferably 37-42° C.

After two days of culture, there is poured over each Petri dish around 20 ml of an agar-based solution prepared as follows: dissolve by heating 15 g of agar in 1 liter of a potassium phosphate buffer solution at 50 mM (pH 6) supplemented with 100 mg/l of bromothymol blue, cool the solution to 50° C., add 10 g of urea and acidify the medium with hydrochloric acid until a yellowish-orange color is obtained.

After solidification of the agar, the Petri dishes are incubated for 1 hour at 37° C.

The ur(+) clones form blue-colored halos owing to the production of ammonia, whereas the ur (−) clones form yellow colonies.

When the ur(−) mutants are sought, the clones not forming a blue halo are recovered and tested again on the same culture medium in order to confirm the ur(−) characteristic. It should also be verified that these mutants do not consume urea (or consume it only partially) when they are cultured in milk.

The term "yellow" in relation to that ur (−) clones form yellow colonies should be understood as the skilled person would understand it in the present context.

As described above—a mutant/clone may consume urea partially and still be what skilled person would measure as an ur (−) clone in this plate assay of this Example 1. Accordingly, it may be that the color of a specific mutant/clone could be what may be termed light green—i.e. a color that it clearly significantly closer to yellow than blue—such a clone would by the skilled person be understood as a ur (−) clone in the present context.

Example 2

S. thermophilus ur(−) Bacteria—LESS Floating Cheese Curd Problems

S. thermophilus strain CHCC9908 was isolated as a urease negative ur(−) mutant from the ur(+) wildtype S. thermophilus strain CHCC4325/ST 3.

Both the ur(−) and the ur(+) strain may be obtained upon request to Chr. Hansen A/S, Denmark.

The CHCC9908 ur(−) and the ur(+) wildtype CHCC4325 strains were used to make cottage cheese according to a standard procedure for making cottage cheese.

Everything was equal in the two experiments—only difference was that in one experiment was used the ur(−) strain and in the other experiment was used the ur(+) strain—i.e. it was a true comparison between use of ur(−) and ur(+).

The results of the acidification profile/kinetics are shown in table 2 below.

TABLE 2

| After inoculation [min] | Numerical time | | | | | | | |
|---|---|---|---|---|---|---|---|---|
| | Vat 404 ST-9908 ur(−) | | | | vat 407 ST-3 ur(+) | | | |
| | Time | pH | pH drop | Total | Time | pH | pH drop | Total |
| 0 | 06:00 | 6.56 | 0 | 0 | 06:15 | 6.56 | 0 | 0 |
| 30 | 06:30 | 6.52 | 0.04 | 0.04 | 06:45 | 6.5 | 0.06 | 0.06 |
| 60 | 07:00 | 6.47 | 0.05 | 0.09 | 07:15 | 6.48 | 0.02 | 0.08 |
| 90 | 07:30 | 6.36 | 0.11 | 0.2 | 07:45 | 6.4 | 0.08 | 0.16 |
| 120 | 08:00 | 6.25 | 0.11 | 0.31 | 08:15 | 6.28 | 0.12 | 0.28 |
| 150 | 08:30 | 6.07 | 0.18 | 0.49 | 08:45 | 6.1 | 0.18 | 0.46 |
| 180 | 09:00 | 5.83 | 0.24 | 0.73 | 09:15 | 5.88 | 0.22 | 0.68 |
| 210 | 09:30 | 5.49 | 0.34 | 1.07 | 09:45 | 5.61 | 0.27 | 0.95 |
| 240 | 10:00 | 5.21 | 0.28 | 1.35 | 10:15 | 5.24 | 0.37 | 1.32 |
| 270 | 10:30 | 4.97 | 0.24 | 1.59 | 10:45 | 4.97 | 0.27 | 1.59 |
| 300 | 11:00 | 4.78 | 0.19 | 1.78 | 11:15 | 4.8 | 0.17 | 1.76 |
| 330 | 11:30 | 4.63 | 0.15 | 1.93 | 11:45 | 4.68 | 0.12 | 1.88 |
| 360 | 12:00 | | | | 11:55 | 4.64 | 0.04 | 1.92 |

As can be seen from table 2—the acidification profile/kinetics for the ur(−) and ur(+) may be seen as similar.

In FIG. 1 herein is shown the cottage cheese vat made with the urease-negative mutant CHCC9908.

In this cottage cheese vat (shown in FIG. 1), produced with the urease-negative mutant CHCC9908, we measured the cheese curd depth both in the middle and at the corners, and it was 7-8 cm below the whey surface at both places.

In FIG. 2 herein is shown the cottage cheese vat made with the ur(+) strain -i.e. the control vat.

In the control cottage cheese vat—made with the ur(+) strain and shown in FIG. 2—the cheese curd was right at the surface of the whey in the corners, and in the middle it was about 2.5 cm below the surface.

Conclusions

This example clearly demonstrated that the *S. thermophilus* urease negative ur(−) mutant CHCC9908 had a very positive impact on the floating curd issue.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. U.S. Pat. No. 6,962,721B1 (Texal, FR)
2. U.S. Pat. No. 3,298,836 (published 1967)
3. WO91/00690A1
4. The article ("Gold Spot Dairy boost cottage cheese sales", Dairy and Ice Cream Field, vol. 156, no. 6, 1973, pages 46-47).
5. U.S. Pat. No. 5,116,737
6. R. Scott, (1986), Cheesemaking process, second ed., Elsevier Applied Science Publishers, London and New York.
7. G. Bylund, (1995), Dairy processing handbook, Tetra Pak Processing Systems, Lund, Sweden
8. F. Kosikowski, (1982), Cheese and fermented milk foods, second ed., Kosikowski & Associates, New York All references cited in this patent document are hereby incorporated herein in their entirety by reference.

The invention claimed is:

1. A method for producing cottage cheese comprising:
   (a) inoculating milk with *Streptococcus thermophilus* bacteria that are not able to release ammonia from urea (herein termed *S. thermophilus* ur(−) bacteria);
   (b) fermenting the milk with the bacteria to obtain a coagulum; and
   (c) separating the coagulum into curd and whey,
   wherein the method results in less floating curd than if the milk had been inoculated via a comparable method using a *Streptococcus thermophilus* bacteria that is able to release ammonia from urea.

2. The method of claim 1, wherein the milk is cow milk.

3. The method of claim 1, wherein the milk is inoculated with from $10^4$ to $10^{13}$ cfu/ml of the *S. thermophilus* ur(−) bacteria.

4. The method of claim 1, wherein the fermenting is for 3 to 7 hours.

5. The method of claim 1, wherein the milk is also inoculated with *Lactococcus* bacteria.

6. The method of claim 5, wherein *Lactococcus* bacteria are homofermentative *Lactococcus* bacteria.

7. The method of claim 5, wherein the milk is inoculated with from $10^4$ to $10^{13}$ cfu/ml of *Lactococcus* bacteria.

8. The method of claim 1, wherein the separating is performed after the milk has been fermented to a pH of 4.0 to 5.0.

9. The method of claim 1, further comprising scalding the separated whey and curd.

10. The method of claim 3, wherein the milk is inoculated with from $10^8$ to $10^{12}$ cfu/ml of the *S. thermophilus* ur(−) bacteria.

11. The method of claim 5, wherein the *Lactococcus* bacteria is *Lactococcus lactis* bacteria.

12. The method of claim 7, wherein the milk is inoculated with from $10^8$ to $10^{12}$ cfu/ml of the Lactococcus bacteria.

13. The method of claim 1, wherein the separating comprises cutting the coagulum into the whey and curd.

14. The method of claim 9, wherein the scalding comprises heating with a steam injector positioned below the surface of the whey and above the curd.

* * * * *